(12) United States Patent
Stringer

(10) Patent No.: US 6,254,895 B1
(45) Date of Patent: Jul. 3, 2001

(54) FAIRY RING CONTROL

(75) Inventor: Glade W. Stringer, Boulder, MT (US)

(73) Assignee: Omega Resources, LLC, Boulder, MT (US)

( * ) Notice: Subject to any disclaimer, the term of this patent is extended or adjusted under 35 U.S.C. 154(b) by 0 days.

(21) Appl. No.: 09/654,296

(22) Filed: Sep. 1, 2000

(51) Int. Cl.$^7$ .......................... A01N 59/00; A01N 59/06; A01N 37/36; A01N 63/00; A01N 25/14
(52) U.S. Cl. .......................... 424/717; 424/715; 424/716; 424/529; 424/44; 424/46; 424/405; 424/489; 514/574; 514/951
(58) Field of Search ...................................... 424/715–717, 424/529, 44, 46, 405, 489; 504/101; 514/574, 951; 71/17

(56) References Cited

U.S. PATENT DOCUMENTS

| | | | |
|---|---|---|---|
| 1,560,558 | * 11/1925 | Fulton et al. | 424/715 |
| 4,599,233 | 7/1986 | Misato et al. | 424/717 |
| 5,330,964 | 7/1994 | Alesi, Jr. | 504/119 |
| 5,432,146 | * 7/1995 | Winston | 504/101 |

* cited by examiner

*Primary Examiner*—John Pak
(74) *Attorney, Agent, or Firm*—Wells, St. John, Roberts, Gregory & Matkin

(57) ABSTRACT

A fairy ring treatment compound is disclosed comprising a bicarbonate salt fungicide and an acid salt. The treatment process includes the step of spreading the compound over vegetation affected by the fairy ring.

9 Claims, 1 Drawing Sheet

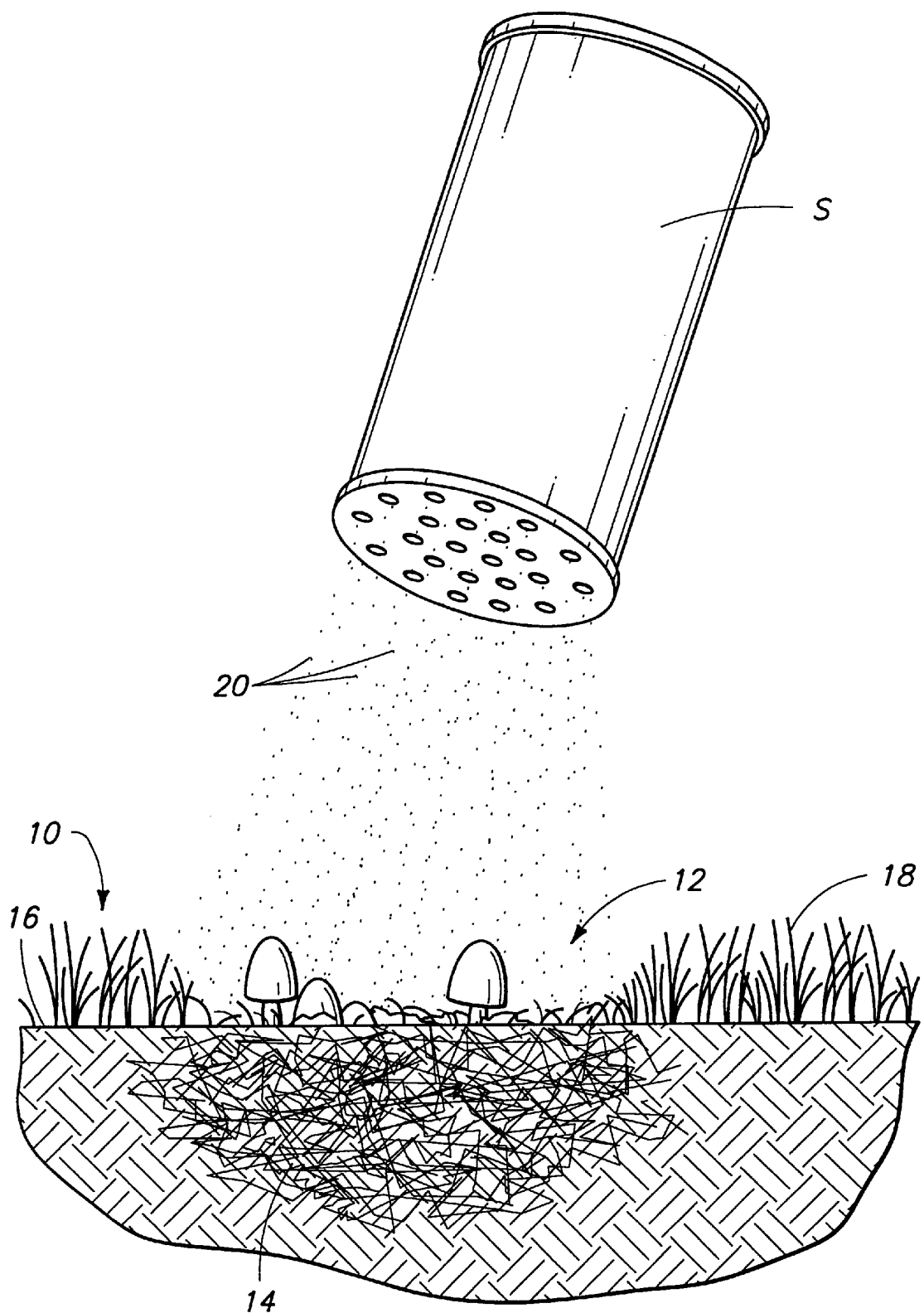

FAIRY RING CONTROL

TECHNICAL FIELD

The present invention relates to treatment of fairy rings.

BACKGROUND OF THE INVENTION

Fairy rings are a feared but common turf malady caused by growth of mushroom forming fungus. The growth occurs most usually in areas where there are high concentrations of lignin. Sawdust, buried logs or timbers, decorative bark or wood chips that have been tilled under, will often eventually encourage fungal growth that can result in fairy rings.

Many extension agents, horticulturists, plant treatment specialists and others recommend treatment of fairy rings to include excision or removal of effected soil to a depth of 12", followed by replacement with fresh top soil and re-seeding. Others suggest rigorous tillage to similar depths, followed by heavy irrigation and fertilizer treatment. Still others suggest chemical treatment, using flutolanil (a benzanilide fungicide) or methyl bromide. Complete soil sterilization may result from herbicidal treatment and remediation of the soil may not be possible for a period of years.

Part of the difficulty experienced with fairy rings is that the "cobwebby" root structure of the fungus, called mycelium, saps the soil of nutrients and blocks effective passage of water to other plant roots. The surrounding turf will thus die away.

From the above, it may be understood that there has been a long-felt, but substantially unfulfilled, need for an effective treatment of fairy rings.

It has been known, as suggested in U.S. Pat. No. 5,330,964, that bicarbonate of soda can be used as a herbicide. The '964 patent suggests placement of a heavy layer (between ⅛ and ¼ inches) of soda on undesirable plants such as moss, poison ivy, clover, grasses and others. Such a heavy coating on the plants and surrounding soil will undoubtedly destroy the coated plants; but for practical purposes, the amount of material stated as necessary to cause a herbicidal action appears to be impractical, and regeneration of plant life in the treated areas is significantly delayed.

The specification in the '964 patent states that in tests where an initial coating of ⅛ inch of soda was applied, no new vegetation growth occurred in the treated area for a period of two years and that longevity of growth control is a function of the coating thickness. A statement is made that thinner coatings of less than ⅛ inch may be used for shorter periods of controlled new growth, but no reduced thickness is disclosed and results are admittedly speculative.

The '964 patent also discusses application of an aqueous solution of one part water to one part soda as an alternative to powder coating, though application rates are not disclosed apart from a general statement that the solution should be sprayed to an extent that the unspecified, unwanted vegetation is "soaked". No specific discussion is made in the patent regarding control of fairy rings or fungus.

U.S. Pat. No. 4,599,233 discloses a fungicide and fruit storage disease-preventing agent which includes sodium bicarbonate and a food emulsifier surfactant. Specific examples are listed, with various specific surfactants used to treat fungus growth on plants. The compound is thus used to treat growth of fungus on living or harvested plants as opposed to an herbicidal action on the plants themselves.

Neither of the above patents disclose a substantially exclusive treatment for fairy rings.

A coating as suggested in the '964 can be used to destroy vegetation, and therefore could be used to destroy fairy rings. However, the coating thicknesses suggested will result in destruction of adjacent coated vegetation and re-growth will be prevented for unacceptably long periods. Thus, the treatment disclosed in the '964 patent may be effective as a general herbicide, but would not be an attractive solution in areas where part of the plant growth is not to be destroyed, for example in turf where fairy rings occur in the midst of otherwise healthy, desirable vegetation.

No fairy ring treatment is specifically suggested in the '233 patent. Further, it is not likely that the disclosed fungicide treatment (which is used only to control fungus growth on plants) would destroy subsurface mycelium. No destruction of undesired fairy rings would likely result from use of the '233 fungicide.

Thus, a need remains for an effective treatment specific to the problem presented by fairy rings and the adverse effects produced by soil nutrient robbing mycelium found in the soil under fairy rings.

BRIEF DESCRIPTION OF THE DRAWINGS

Preferred embodiments of the invention are described below with reference to the following accompanying drawings.

The single FIGURE is a pictorial view illustrating application of the present fairy ring treatment compound and process for application.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

A section of turf 10 affected by a fairy ring 12 is illustrated in the drawing. The destructive part of a fairy ring is fungus that forms a dense layer of mycelium 14 several inches below the soil surface 16. The mycelium 14 depletes nutrients in the soil at the expanding edge of the ring (which is torroidal in shape), and prevents air and water from reaching adjacent vegetation 18. The result is yellowed or dead vegetation in areas adjacent the ring. The present treatment compound and process is intended to destroy fairy rings without requiring removal or heavy tillage of the adjacent soil.

The present treatment includes a safe and effective compound and process for treating and controlling fairy rings, that may be used to destroy fairy ring fungus along with the underground mycelium while enabling and supporting remediation of the soil and adjacent desirable plant life. The component parts of the present treatment allow for eradication of the fungus and remediation of the adjacent soil in an ecologically safe and effective manner, without requiring excision of the soil or deep tillage.

In one general aspect, the present fairy ring treatment includes a bicarbonate salt and an acid salt mixed with the bicarbonate salt in a dry compound.

In another general aspect, the present fairy ring treatment compound is comprised of a bicarbonate salt fungicide, an acid salt combined with the fungicide, and a soil remediation agent combined with the fungicide and acid salt. The treatment compound when applied to a fairy ring will permeate adjacent affected soil to destroy the fairy ring and enable remediation of the affected soil without requiring tillage.

Another aspect includes a process for treating fairy rings comprising the steps of obtaining a dry compound of bicarbonate salt and an acid salt, and spreading the dry compound over vegetation affected by the fairy ring.

In more specific aspects, the present fairy ring treatment compound is generally designated at 20 in the drawing. In preferred forms, the treatment compound 20 is a dry compound that can be easily applied to vegetation affected by a fairy ring, and to the soil surface 16 in the vicinity.

Generally, the predominant ingredient (by weight) in the compound is a bicarbonate salt. Of the known salts, sodium bicarbonate (also known as bicarbonate of soda) is presently believed to be the most ecologically acceptable and effective and is presently preferable for destroying the various mushrooms found in fairy rings, and more importantly, the sub-surface mycelium 14.

It is preferred that the bicarbonate salt comprise more than 90% by weight of the compound. In more specific forms, the salt occupies approximately 91% by weight of the compound.

The bicarbonate salt is preferably provided in a dry, powdered form that may be easily dry-mixed with other ingredients, preferably a dry acid salt, and a dry soil remediation agent.

The acid salt is preferably a dry, organic carboxylic acid. Most preferably, the acid is a citric acid provided in an anhydrous powder form. Citric acid is also a safe and ecologically acceptable ingredient in the treatment and is used primarily to react with the bicarbonate salt to create a frothing action when contacted with water.

It is preferred in general that the acid occupy approximately 3% of the compound by weight. The acid in this concentration has been found to facilitate the frothing action of the compound when contacted with water, to better facilitate coating the fungus surfaces, while also permitting penetration of the compound into soil to the depth of the mycelium 14.

The soil remediation agent is present in preferred forms of the invention, and generally occupies approximately 6% of the compound by weight. More specifically, the preferred agent is a fertilizer including nitrogen, phosphorous and potassium. The preferred ecologically acceptable agent is dried blood or, more specifically, spray dried blood.

It has been found that the remediation agent is most preferably used as a dry powder, mixed with the bicarbonate salt and acid salt. The agent has been found to assist regeneration and rehydration of the soil in fairy ring affected areas. Remediation of the affected soil with the agent will result in an much more healthy environment for the adjacent vegetation, and regrowth or rejuvenation of the previously affected vegetation will typically occur quickly (usually within a matter of weeks) with normal irrigation.

THE PROCESS

In the process for treatment of fairy rings, the steps involved include generally obtaining a dry compound of sodium bicarbonate and acid salt, then spreading the dry compound over vegetation affected by the fairy ring.

In more specific preferred steps, the compound obtained is a dry powder including the bicarbonate salt, the acid salt, and soil remediation agent, with all three ingredients in proportions as disclosed above.

In one process aspect, the user first wets the affected vegetation. This step is preferred so the applied compound will adhere to the moist surfaces. Once the acid and bicarbonate salt become exposed to water, a frothing reaction will take place and the vegetation will be thoroughly covered with the compound. It is not necessary to saturate the affected area, but simply to moisten the affected area to improve surface adhesion of the compound.

In a preferred step, the compound is spread over vegetation affected by the fairy ring at an application rate of approximately 1 pound of compound per 10 square feet of ground surface. This application rate has been found to be especially effective for fairy ring treatment, and may be accomplished by hand using a shaker S as generally indicated in the drawing. This application rate produces a concentration of the compound on the affected area that will not destroy desired vegetation, but yet allows the compound to attack the fairy ring fungus.

In a preferred step, the compound is sprinkled on the vegetation affected by the fairy ring and on adjacent soil surfaces within a distance of approximately 8 inches from the vegetation affected by the fairy ring. This assures penetration to mycelium tendrils that may extend beyond and below the visibly affected area.

After spreading the compound, the treated area may be left for a period of about 4 hours to allow the compound time to attack and begin destroying the surface fungus. After this period, a further preferred step is to irrigate the vegetation and adjacent soil surfaces. This enables the compound to soak into the soil and destroy the sub-surface mycelium.

It has been found that fairy rings treated with the present compound have disappeared completely and the affected vegetation will quickly rejuvenate within a period of weeks. This is accomplished without requiring tillage or removal of the affected soil. Further, the compound is environmentally safe and will not endanger other plant life, animals, or aquifer.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A process for treating fairy rings comprising the steps of:
   wetting a vegetation locus affected by a fairy ring;
   obtaining a dry composition consisting essentially of (i) 90 wt % or more of a bicarbonate salt in powder form, (ii) a salt of citric acid in powder form in an amount sufficient to create a frothing action with said bicarbonate when contacted with water, and (iii) dried blood in powder form in an amount sufficient to function as a soil remediation agent; and
   spreading an effective fairy ring controlling amount of the dry composition over said locus.

2. The process of claim 1 wherein the dried blood comprises approximately 6% of the composition by weight.

3. The process of claim 1 wherein the composition contains approximately 3% of the salt of citric acid by weight.

4. The process of claim 1 wherein the composition is comprised of:
   approximately 91% sodium bicarbonate by weight;
   approximately 6% dried blood by weight; and approximately 3% salt of citric acid by weight.

5. The process of claim 1 wherein the step of wetting the vegetation locus is accomplished prior to the step of spreading the dry composition.

6. The process of claim 1 comprising the further step of:
   irrigating the locus after the step of spreading the dry composition.

7. The process of claim 1 wherein the step of:
   wetting the locus is accomplished prior to the step of spreading the dry composition and includes the further step of
   irrigating the locus and the composition spread thereon after approximately 4 hours from the spreading step.

8. The process of claim 1 wherein the spreading step is accomplished at a rate of approximately 1 pound of composition for each 10 square feet of locus to be treated.

9. The process of claim 1 wherein the spreading step is comprised of:
   sprinkling the composition on the locus and on adjacent soil surfaces within a distance of approximately 8 inches from the locus affected by the fairy ring.

* * * * *